(12) United States Patent
Wenzler et al.

(10) Patent No.: US 6,406,475 B1
(45) Date of Patent: Jun. 18, 2002

(54) PIVOTING DEVICE FOR PIVOTABLE PARTS OF BIPOLAR ELECTROSURGICAL EQUIPMENTS

(75) Inventors: Peter Wenzler, Frittlingen (DE); Philip Eggers, Dublin; Andrew Eggers, Ostrander, both of OH (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/363,326

(22) Filed: Jul. 28, 1999

(30) Foreign Application Priority Data

Jun. 29, 1998 (DE) .......................... 198 28 976

(51) Int. Cl.⁷ .............................................. A61B 18/18
(52) U.S. Cl. .............................. 606/48; 606/50; 606/51
(58) Field of Search .............................. 606/46, 48, 50, 606/51, 52

(56) References Cited

U.S. PATENT DOCUMENTS

| 3,651,811 A | 3/1972 | Hildebrandt et al. |
| 5,324,289 A | 6/1994 | Eggers |
| 5,569,243 A | * 10/1996 | Kortenbach et al. ........... 606/46 |
| 5,697,949 A | * 12/1997 | Giurtino et al. ............. 606/205 |
| 5,976,132 A | * 11/1999 | Morris ......................... 606/49 |
| 6,063,086 A | * 5/2000 | Benecke et al. ............... 606/51 |

FOREIGN PATENT DOCUMENTS

| EP | 0 572 131 A1 | 12/1993 |
| EP | 0 589 453 A2 | 3/1994 |

* cited by examiner

*Primary Examiner*—Linda C. M. Dvorak
*Assistant Examiner*—David M. Ruddy

(57) ABSTRACT

A pivoting device the two electrically conductive arms (12, 14) of which are connected pivotably by a screwed joint (16) having a screw (46) and a nut (74). Surfaces (26, 28) of the arms (12, 14) which rest against one another, and also the pivoting device (16), are electrically insulated. The nut (74) has, at least in part, a noncircular, preferably elliptical, smooth circumferential surface (80). Holes (36, 38) in the two arms (12, 14) for accommodating the screwed joint (16) are designed in such a way that, in the assembled state, the screw (46) and the nut (74) are arranged in a recessed manner in the holes (36, 38). Electrically insulating material is provided at least in the region of the surface of the screw (46) and the nut (74) and/or the inner walls of both holes (36, 38) in the scissor arms (12, 14).

26 Claims, 3 Drawing Sheets

PIVOTING DEVICE FOR PIVOTABLE PARTS OF BIPOLAR ELECTROSURGICAL EQUIPMENTS

TECHNICAL FIELD

The invention relates to a pivoting device for pivotable parts of bipolar electrosurgical equipments in accordance with the preamble of claim 1.

BACKGROUND OF THE INVENTION

One of the main problems during surgical interventions is rapidly and reliably stemming any bleeding which may occur. Bleeding occurs particularly during the cutting or removal of tissue by means of surgical cutting instruments. In order to achieve rapid hemostasis, there are already surgical techniques known in which the surgical scissors used to remove or cut the tissue are provided with devices for stanching bleeding. Thus, use is made in surgical interventions of f.i. bipolar electosurgical scissors whose scissor arms can be connected to a high-frequency voltage source and are suitable not only for cutting through tissue or blood vessels but also for the preferably simultaneous sealing of blood vessels by electrocoagulation. It is of course important when designing such electrosurgical scissors that the high-frequency current should flow exclusively through the desired area of tissue and that no short circuits occur between the scissor arms.

In order to ensure the necessary electrical insulation between the scissor arms of a bipolar electosurgical instrument, the proposal in the genus-forming U.S. Pat. No. 5,324,289, is to provide at least one of the two scissor surfaces which rest against one another in the closed state with an electrical insulating layer. In order furthermore also to prevent electrical short circuits via the pivoted connection between the two scissor arms, this pivoted connection is configured either as a riveted joint produced from an electrically insulating material or as a screwed joint. In this case, a screw is screwed through one scissor arm into the other scissor arm. The screw is composed of electrically insulating material, or the screw is shielded electrically from one of the two scissors arms by a sleeve composed of electrically insulating material.

U.S. Pat. No. 3,651,811 has likewise disclosed a pivoting device for the two scissor arms of a bipolar electrosurgical pair of scissors, said device comprising a screwed joint in which a screw composed of metal is electrically insulated from a scissor arm through which it is inserted by a sleeve produced from insulating material. EP-A-0 589 453 furthermore proposed a riveted pivoting device between the two scissor arms, this pivoting device likewise being decoupled electrically from the scissor arms by an insulating sleeve.

The known pivoting devices are configured in such a way that they project beyond the outer surfaces of the two scissor arms, with the result that the tissue of a patient may be damaged during an operation. With the screwed joints used, there is furthermore the risk that the screw will come loose and the fit between the two scissor arms will thus be loosened. The internal thread in one scissor arm makes the production of the scissors uneconomical. When using a riveted joint for the pivot joint of the arms of bipolar electrosurgical scissors, on the other hand, the maintenance or replacement of a defective scissor arm is difficult since it is necessary for this purpose to pry the riveted joint open. With riveted joints there is furthermore the risk that the press fit achieved between the two scissor arms will be inadequate or excessive, and this can lead to impairment of handling and of the cutting ability of the scissors.

DISCLOSURE OF THE INVENTION

It is an object of the invention to avoid the above-mentioned disadvantages and to propose a pivoting device for pivotable parts of bipolar electrosurgical equipments which is simple to produce and maintain and reliably prevents a short-circuiting link between the pivotable parts via their pivoting device.

This object is achieved by means of pivoting device having the features specified in claim 1. Advantageous developments of the invention are specified in the dependent claims.

According to the invention, the pivoting device for bipolar electrosurgical equipments has two electrically conductive pivotable parts, each of which is (provided with a cutting edge and which) is connected pivotably to one another by said pivoting device and those surfaces of the two pivotable parts which rest against one another being electrically insulated from one of the parts. The pivoting device is a screwed joint which comprises a screw and a nut. A hole is provided in one of the two parts for the recessed accommodation of the screw, and a further hole is provided in the other of the two parts for the recessed accommodation of a nut of the screwed joint. An electrically insulating material is provided at least in/on the surfaces of the screw and the nut and/or in/on the surfaces of the holes in the two pivotable parts.

According to a first embodiment, the nut can be provided at least in part with a smooth circumferential surface of noncircular form. The noncircular but regular smooth circumferential surface of the nut not only ensures that no twisting of the screwed joint occurs as it is tightened but also ensures an accurate fit in the hole in the pivotable part, a fit which takes account to a high degree of the hygiene requirements and virtually excludes the risk of injury or damage to body tissue or objects.

The design according to the invention of the pivoting device of the two parts of the bipolar electosurgical equipment as a screwed joint ensures reliable and precise relative seating of the pivotable parts and, hence in case of a bipolar electrochirugical scissor, a good cutting operation, since it is possible to adjust the seating of the pivotable parts or scissor arms, respectively, in an optimum manner by means of the tightening torque of the screw, and the screwed joint reliably maintains the setting, once made. The recessed arrangement of the screwed joints in the pivotable parts or scissor arms prevents unintentional injury to the tissue of the patient or catching of or damage to objects, e.g. gauze cloths or latex surgical gloves.

Since the screw and the nut of the screwed joint can be produced from the same material, the risk of undesirable wear is prevented. This can occur when the screw and nut are composed completely or in part of different materials.

A preferred solution is to provide the holes in the pivotable parts of the bipolar electrosurgical equipment in an identical and axially symmetrical manner with respect to one another with respective inner flanges.

In a second embodiment of the invention, the electrical insulation of the screwed joint of the two pivotable parts comprises a two-sleeve insert produced from electrical insulating material, this being particularly advantageous, and, in this arrangement, the inside of one sleeve being formed in positive engagement with the screw head and the inside of the other sleeve being formed in positive engagement with the nut. This configuration of the bipolar electrosurgical pair of pivotable parts likewise simplifies its product ion since the holes in the pivotable parts are of identical design, and only one tool setting is thus required. Above all, electrical insulation by means of an insert comprising two sleeves ensures a particularly high electrical breakdown strength.

As a further development of this particularly preferred embodiment, the underside of the screw head is conically tapered and rests against a correspondingly conically shaped surface of a washer, which is preferably composed of the same material as the screw. This design makes it possible to tighten the screw in a simple and reliable manner since the washer ensures good seating of the screw and prevents premature wear.

Further features and advantages of the invention are explained in greater detail with reference to the attached drawings.

DETAILED DESCRIPTION OF THE PREFERRED EMBODIMENTS

Figure 1:
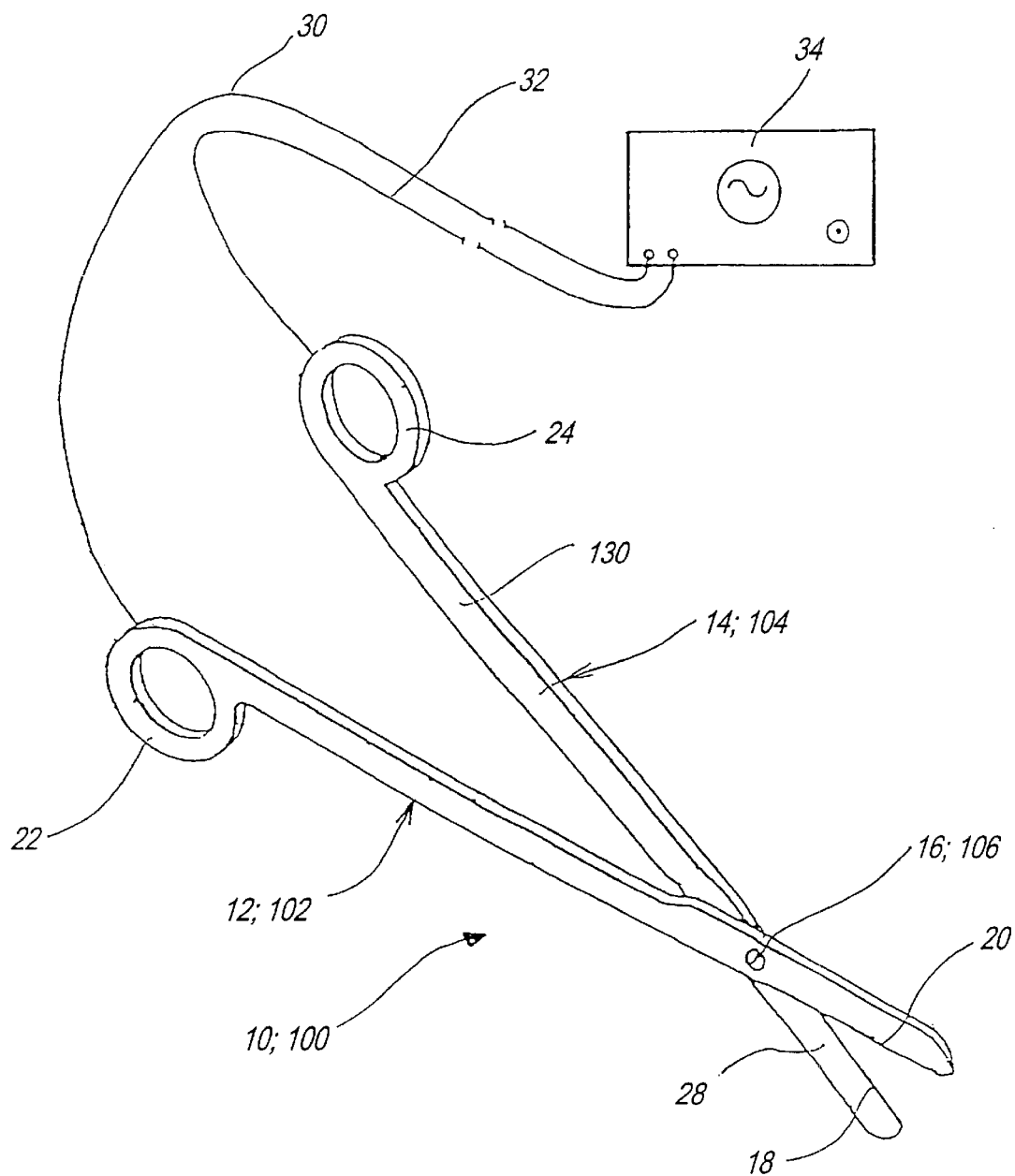
FIG. 1 shows a bipolar electrosurgical pair of scissors in a diagrammatic view.

FIG. 1 shows a bipolar electosurgical equipment defining a pair of scissors 10 and two pivotable parts forming scissor arms 12, 14 which are connected pivotably to one another by said pivoting device 16 and each have a cutting edge 18, 20 at the front end and an annular gripping element 22, 24 at the rear end. In the region of a dividing plane T (FIGS. 2A and 3A) between the two scissor arms 12, 14, their cutting surfaces 26 and 28 lie opposite one another, and of these only the cutting surface 28 of scissor arm 14 can be seen in FIG. 1. The scissor arms 12, 14 form two electrodes for electrocoagulation and, for this purpose, are connected at the gripping elements 22, 24 to a high-frequency voltage source 34 via separate leads 30, 32 respectively. The two scissor arms 12, 14 are manufactured from an electrically conductive material, preferably stainless steel or an aluminum compound, and are provided, at least on the cutting surfaces 26, 28 which rest against one another, with an electrically insulating layer, which is known per se and is therefore not shown, in order to prevent an unwanted short circuit between the scissor arms 12, 14. The insulating layer can be manufactured from an inorganic, electrically insulating material such as glass, ceramic, nitride, boride or synthetic diamond, it being possible, in addition, for materials of great hardness, which have good cutting properties, to be used for the cutting edges 18, 20.

Figure 2A:
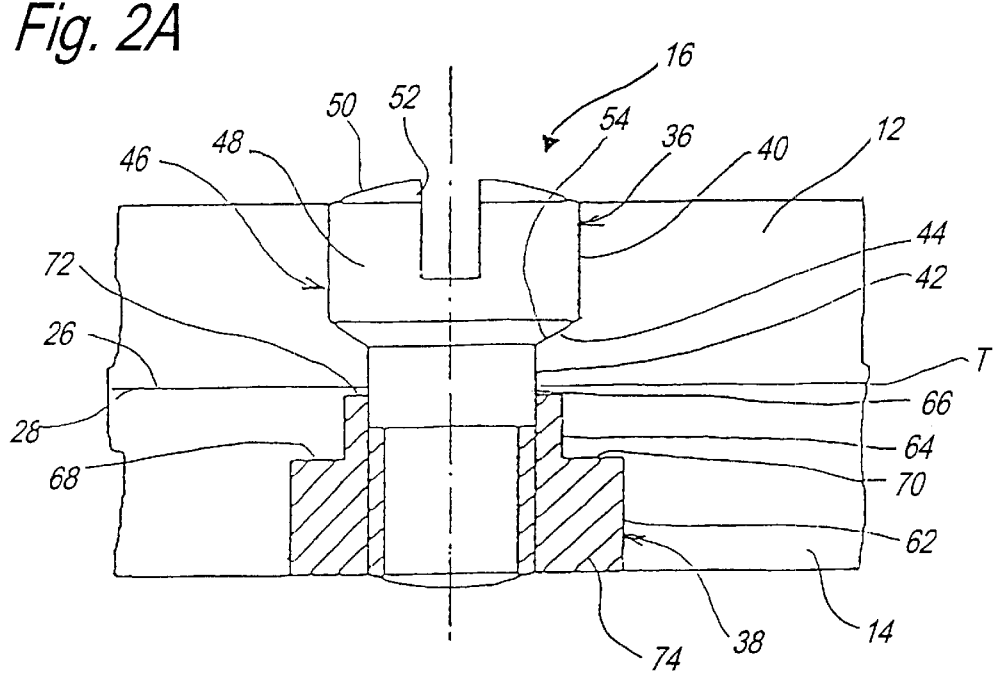
FIG. 2A shows a cross section through a first embodiment of a pivoting device for a bipolar electosurgical pair of scissors in accordance with the invention.

According to FIG. 2A, the two scissor arms 12, 14 are of approximately equal thickness in the region of the pivoting device 16 and have coaxial through holes 36, 38 in the region of the pivoting device 16.

The hole 36 in one scissor arm 12 has an outer, circular-cylindrical hole section 40 of larger diameter, the inner end of which merges into a coaxial, circular-cylindrical hole section 42 of smaller diameter, which has an annular shoulder 44 on the upper side. The annular shoulder 44 is widened outwards in the form of a truncated cone on its upper side, at an angle of about 30°, while the underside of the annular shoulder 44 is formed by the cutting surface 26 of the scissor arm 12. The hole sections 40 and 42 of the hole 36 in one scissor arm 12 correspond approximately to the dimensions of a screw 46.

Figure 2B:
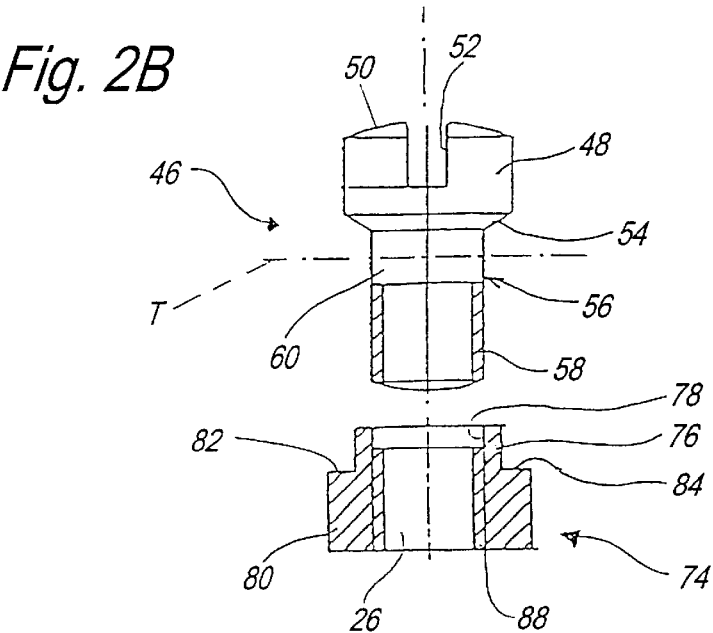
FIG. 2B shows an exploded view of the pivoting device in accordance with the first embodiment.

According to FIG. 2B, the screw 46 has a cylindrical screw head 48, which is provided at its outer end 50 with a diagonal actuating groove 52 for the insertion of a screwdriver and, on its underside, with an annular surface 54 which, towards the outside and towards its outer edge, is of frustoconical configuration to match the annular shoulder 44 (FIG. 2A) of the hole 36. The screw 46 furthermore has a screw shank 56 with an external thread 58 and a smooth cylindrical shank section 60, the upper end of which is bounded by the annular surface 54 of the screw head 48 and the lower end of which is bounded by the external thread 58. According to FIG. 2A, the smooth-walled shank section 60 extends right into the upper end of the hole 38 in the scissor arm 14, over a length corresponding approximately to one quarter of the length of the hole 38. The screw head 48 is accommodated with a tight fit by hole section 40 of scissor arm 12 and can be sunk almost completely into it, eliminating the risk of injury or damage to tissue or objects. Instead of the groove 52, a cross slot or a polygonal hole can be provided on the upper side of the screw head 48 for the insertion of a screwdriver.

According to FIG. 2A, the hole 38 in the other, lower scissor arm 14 is of different design to the hole 36 in the upper arm 12. It has an outer, larger hole section 62 with a cross section which is not circular and which is preferably elliptical and smooth-walled. The elliptical hole section 62 is bounded by two shoulders 68, 70 which lie diagonally opposite one another and are formed in the region of the ends of the major axis x of the elliptical cross section of the hole section 62. The hole 38 continues in a central, circular-cylindrical hole section 64 with an, in comparison, smaller diameter and in an inner hole section 66 with a diameter which is matched to that of the screw shank 60. The central hole section 64 ends in an, in comparison, considerably narrower inner annular shoulder 72 of very small height in hole section 66, the end situated opposite the annular shoulder 72 being formed by the cutting surface 28 of the scissor arm 14. This two-stage hole 38 serves for the tight-fitting positive acceptance of a nut 74.

Figure 2C:
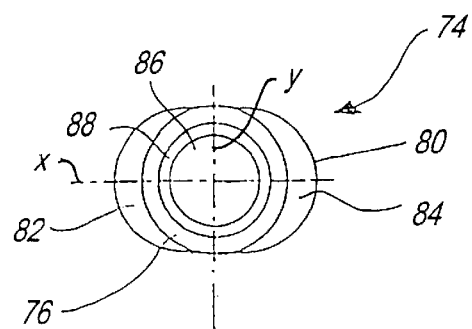
FIG. 2C shows a side view of a nut for the pivoting device in accordance with the first embodiment.

FIGS. 2B and 2C, in particular, show that the nut 74 has a circular-cylindrical length 76 at the front, which is smooth-walled on the inside and outside and the dimensions of which correspond approximately to the central hole section 64 of arm 14 in FIG. 2A. An inner-wall section 78 with a smooth surface extends from the front end of the length 76 into the interior approximately half way along the length 76 where the external thread 58 of the screw 46 begins in the installed state of the latter in FIG. 2A in order thereby additionally to make current transfer impossible. According to FIG. 2C, a rear length 80 of the nut 74 has a shape which is not circular, preferably being elliptical, with a smooth circumferential surface which corresponds approximately to that of hole section 62 in scissor arm 14, so that an outer end 75 of the nut 74 ends flush with the outside of scissor arm 14. Between each of these lengths 76, 80 of the nut 74 there is therefore a respective shoulder 82, 84, these extending diametrically towards opposite sides and are formed by the ends of the length 80 of elliptical cross section, which project beyond the circumference of the circular-cylindrical length 76. The shape of the nut 74 in this first embodiment, which is not circular, preferably being elliptical, serves not only to secure it against twisting but also, to a high degree, meets hygiene requirements since it does not have any recesses, which could be subject to soiling, or projecting edges which could catch and possibly damage the tissue of the patient or other objects.

The nut 74 has a circular-cylindrical internal through hole 86, which is provided with an internal thread 88 whose length is matched to the external thread 58 of the screw shank 56. The internal thread 88 preferably extends only as far as the smooth-walled inner-wall section 78, as FIG. 2B shows, in order to allow not only easy insertion of the screw shank 56 into the nut 74 but, above all, as mentioned, to prevent a current transfer.

In order to prevent a short-circuiting link between the two electrically conductive scissor arms 12, 14 via the pivoting device 16, there is, on the one hand, the possibility of producing the screw 46 and/or the nut 74 of the pivoting device 16 from a nonconductive material or of providing those surfaces of the screw 46 and/or of the nut 74 which rest against the walls of the hole with an electrically insulating coating. By way of example, said electrically insulating coating may be selected from group including glasses, ceramics, glass ceramics, metal oxides, metal nitrides, metal borides and synthetic diamond. It is particularly advantageous here to manufacture at least part of the pivoting device 16 from an aluminum material, especially $AlMgSi_{0.5}$ and to surround its surface with an electrically insulating protective shell by means of hard-anodic oxidation, in which aluminum oxide is formed. A surface treatment of this kind has the advantage of a permanent insulating effect and high wear and corrosion resistance. In addition, high heat resistance is achieved, this being far above the sterilization temperature of 134° C. for medical equipment. Moreover, the biocompatibility stipulated for medical equipment is guaranteed. However, the pivoting device 16 can also be produced from a bioceramic material which has similar properties. Zirconium oxide is particularly suitable here, though polyetheretherketone is also suitable. However, inorganic electrically insulating materials such as glass/ceramic (e.g. Pyroceram (™), a trade mark of Corning Glass Works, Corning, N.Y.), metal oxides (e.g. aluminum oxide), metal nitrides (e.g. silicon nitride, metal boride), or synthetic diamond can be used, as can a plastic containing a, for example, powdered insulating material. For the purpose of the present invention, the term "electrically insulating" is defined as any material or coating whose bulk electrical resistivity is greater than about $10^6$ Ohm/cm and/or whose electrical resistance across an electrically insulating layer is greater than about 10,000 Ohm.

To prevent a short-circuiting link via the pivoting device 16, there is furthermore the possibility of providing the walls of the holes 36, 38 provided to accommodate the pivoting device 16 in the arms 12, 14 with an electrically insulating material. The same materials, as given above, with electrically insulating properties as for the production of the electrically insulating pivoting device 16 are suitable in principle in this case. Where the electrical insulation is to be achieved by lining the walls of the holes in the scissor arms 12, 14, the pivoting device 16 can be manufactured from metal, this leading to low production costs for the screwed joint. Both where the pivoting device 16 is itself of electrically insulating design and where it is made of metal, the production of the screw 46 and the nut 74 from the same material ensures that there is no abrasion when the screw 46 is tightened, this being undesirable particularly with medical equipment.

In FIG. 1, a second particularly preferred embodiment of a bipolar surgical pair of scissors 100 is again made up of two scissor arms 102, 104 which are connected pivotably to one another by a pivoting device 106 and are protected from short-circuiting by an insert 144 made of electrically insulating material.

Figure 3A:
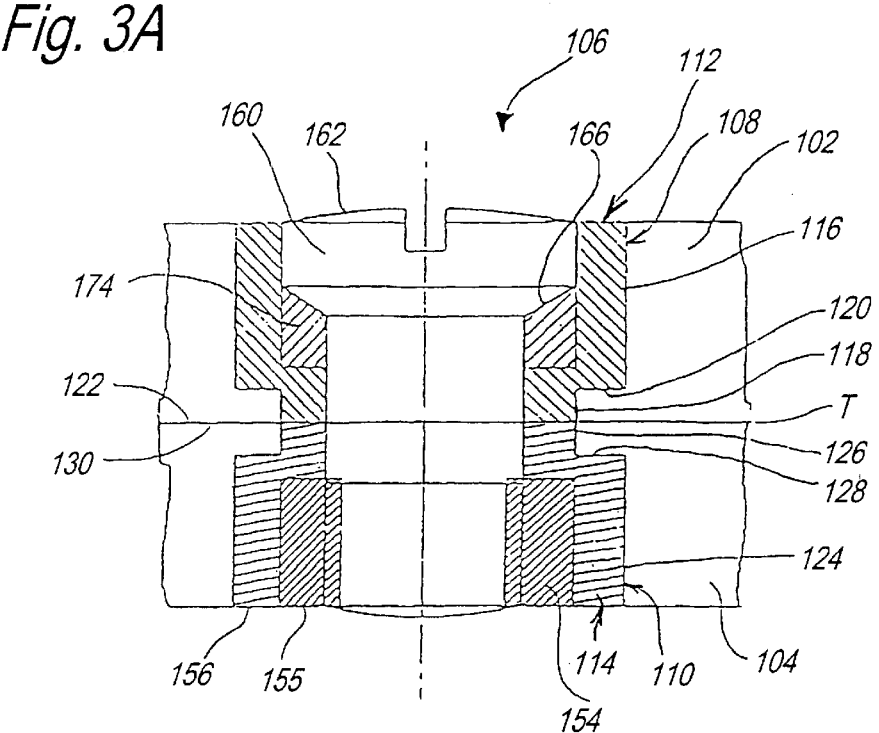
FIG. 3A shows a cross section through a second embodiment of a pivoting device for a bipolar electosurgical pair of scissors in accordance with the invention.
Figure 3B:
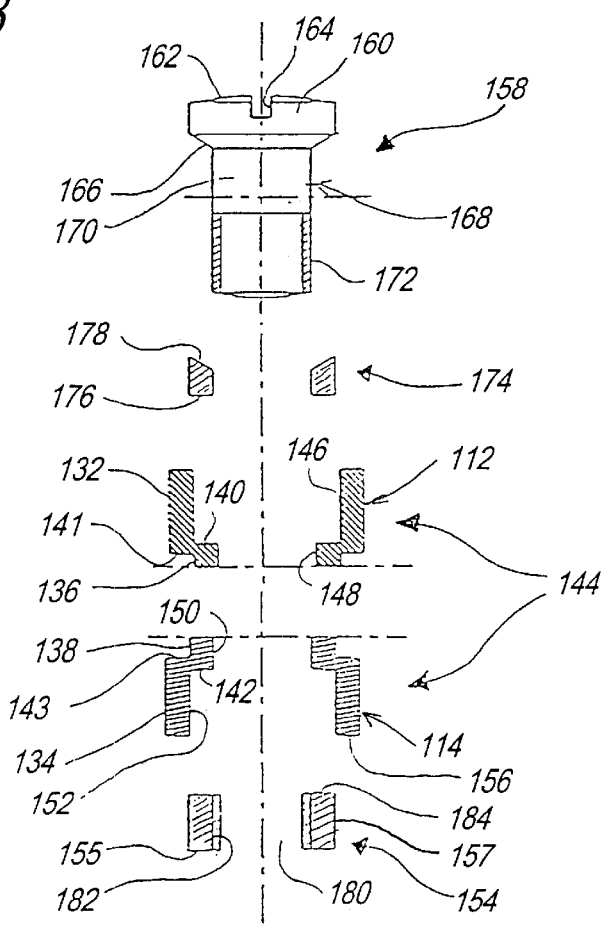
FIG. 3B shows an exploded representation of the pivoting device in accordance with the second embodiment.

According to FIGS. 3A and 3B, this pair of scissors 100 again has scissor arms 102, 104 of equal thickness with coaxial through holes 108 and 110 for accommodating the pivoting device 106, the two holes 108, 110 having identical dimensions. The holes 108, 110 serve to accommodate the insulating insert 144, which in each case comprises a sleeve 112, 114 with outside dimensions corresponding to the holes 108, 110. This ensures that the widest possible variety of scissor-like instruments, each with the same drilling or cutting tool and with the same sleeves, screws and nuts, can be used to produce the pivoted connection between its parts capable of pivoting relative to one another. Stock holding of the parts to be provided for the pivoted connection and production are thereby simplified and the economic outlay is hence reduced as well.

According to FIG. 3A, the hole 108 in one scissor arm 102 has a circular-cylindrical hole section 116 of larger diameter on the outside, the inner end of this section merging into a coaxial circular-cylindrical hole section 118 of smaller diameter which forms an annular shoulder 120. On its upper side, the annular shoulder 120 has a shoulder surface at right angles to the axis of the pivoting device 106, while the underside of the annular shoulder 120 is again formed by an inner scissor surface 122, parallel to the latter, on one scissor arm 102.

In contrast to the first embodiment in FIGS. 2A–2C, the hole 110 in the other, lower scissor arm 104 has, as mentioned, identical dimensions to the hole 108 in the first, upper scissor arm 102, as shown in FIG. 3A. Hole 110 has an outer circular-cylindrical hole section 124 of larger diameter, the inner end of the which merges into a coaxial circular-cylindrical hole section 126 of smaller diameter, thus forming an annular shoulder 128. On its underside, the annular shoulder 128 is likewise right-angled, while the upper side of the annular shoulder 128 is again formed by a right-angled surface 128 of scissor arm 104.

According to FIGS. 3A and 3B, the two sleeves 112, 114 of the insert 144 each have an outer sleeve section 132; 134 with a larger circular-cylindrical outer surface and an inner sleeve section 136, 138 with a smaller circular-cylindrical surface, with the result that an inner right-angled shoulder 140, 142 is in each case formed by the inner sleeve sections 136, 138 and an outer shoulder 141, 143 is in each case formed by the outer sleeve sections 132, 134.

It can be seen from FIG. 3A that the wall thickness of the sleeve sections 132, 134; 136, 138 in each case corresponds approximately to the radial width of the shoulders 120 and 128 in the holes 108, 110 in the scissor arm 102, 104, with the result that the sleeve sections 136, 138 each cover the inner hole sections 118; 126 and their shoulders 120, 128. As a result, those sides of the shoulders 140, 142 of the two sleeves 112, 114 which lie opposite one another in the region of the dividing plane T are in alignment with the dividing plane T of the scissor arms 102, 104, so that the two sleeves 112, 114 together form the insert 144 for the through holes 108, 110 of the two scissor arms 102, 104.

The upper, outer sleeve section 132 of the sleeve 112 has a circular-cylindrical inner wall 146 of larger diameter, and the lower, inner sleeve section 136 has a circular-cylindrical inner wall 148 of smaller diameter. This diameter of the circular-cylindrical inner wall 148 corresponds to the diameter of a circular-cylindrical inner wall 150 of the inner sleeve section 138 of the lower sleeve 114.

The clear cross section of a circular-cylindrical inner wall 152 of the outer sleeve section 134 of the lower sleeve 114 furthermore has a diameter which corresponds to that of the circular-cylindrical inner wall 148 of the upper sleeve section 132 of the sleeve 112. Both sleeves 112, 114 thus have identical dimensions corresponding to the holes 108, 110 in the scissor arms 102, 104 and are accommodated with positive engagement by the holes 108, 110.

FIGS. 3A and 3B furthermore show a screw 158 which has a cylindrical screw head 160 with an outer end 162 and an actuating groove 164. The underside of the screw head 160 again has a frustoconical annular surface 166 which widens outwards and upwards and is adjoined by a screw shank 168 with a smooth-walled shank section 170, which is bounded at the end of the screw shank 168 by an external thread 172. The diameter of the screw head 160 corresponds to the diameter of the circular-cylindrical inner wall 146 of the sleeve 112. The diameter of the screw shank 168 corresponds approximately to that of the inside diameter of the circular-cylindrical inner walls 148, 150 of the sleeve sections 136, 138 of the sleeves 112, 114, thus ensuring a positive engagement between the inner sleeve sections 148, 150 and the screw 158, said positive engagement ensuring electrical insulation.

FIG. 3B shows a nut 154 with a smooth-walled circular-cylindrical outer surface 157 in a central longitudinal section. Since the outside diameter and the height or thickness of the nut 154 correspond to the inside diameter and height of the clear cross section of the cylindrical inner wall 152 of the outer sleeve section 134, the nut 154 can be taken up completely by the sleeve 114 until it rests on the shoulder 142 and is held positively and in a manner secure against twisting by virtue of the frictional or snug fit. An outer end face 155 of the nut 154 is therefore flush with an end 156 of the sleeve 114 and the outside of the arm 104 in the assembled state and thus forms a largely smooth flat surface.

The nut 154 has an internal through hole 180, which is provided with an internal thread 182 matched to the length of the external thread 172 of the screw shank 168. The internal thread 182, like the nut 74 in FIG. 2B, preferably does not extend through the entire internal hole 180 in the nut 154 as far as its inner end 184 in order to allow simple introduction of the screw shank 168 into the nut 154 and to optimize the electrical insulation.

An annular metallic washer 174 in FIGS. 3A and 3B has an outside diameter corresponding to the circular-cylindrical inner wall 146 of the sleeve 112 and an inside diameter corresponding to the inner walls 148, 150 of the inner sleeve sections 136, 138. The radial width of the ring of the washer 174 corresponds to the radial width of the inner shoulder 140 of the sleeve 112. While an underside 176 of the washer 174 lies in a plane at right angles to the axis of the screw and is supported on the inner shoulder 140 of the sleeve 112, an upper side 178 of the washer 174 corresponds to the frustoconical annular surface 166 of the screw head 160, so that the screw head 160 is supported on the washer 174 and is centered by the latter within the sleeve 112. The washer 174 is preferably composed of the same metallic material as the screw 158 in order to avoid abrasion between the two parts, which is undesirable particularly with medical equipment.

Once the sleeve 112 together with the washer 174 has been inserted into the hole 108 in the scissor arm 102, and the sleeve 114 with the nut 154 inserted into its free elliptical sleeve section 134 has been inserted into the hole 110 in scissor arm 104, the screw 158 is pushed through the washer 174 in the sleeve 112 and the inner sleeve sections 136, 138 until the external thread 172 of the screw 158 meets the internal thread 182 of the elliptical nut 154 and the latter is screwed in, tightening the screwed joint. By virtue of the positive configuration of the seating of the nut 154 in sleeve section 134 of sleeve 114, the nut 154 is held secure against twisting in the sleeve 114, so that the inner end faces of the inner sleeve sections 136, 138, said end faces resting against one another in the region of the dividing plane T, are pressed firmly against one another, and the scissor arms 102, 104 can be connected firmly but in a manner which allows them to pivot relative to one another. However, an additional safeguard against twisting of the nut 154 can be achieved by using the nut 74 which is described above and shown in FIGS. 2A and 2C—which is at least in part not circular in cross section, preferably being elliptical—if this is desired because of, for example, the materials used for the various components of the scissors. In this case, the sleeve 114 would have an inner wall 152 of noncircular cross section, which would be matched to the noncircular cross section of the nut 154. Finally, a further safeguard against twisting could be achieved if the outer, larger sleeve section 134 of the sleeve 114 and the outer hole section 124 accommodating it were provided solely or additionally with a noncircular matching cross section. These abovementioned modifications to the second embodiment of the invention which has been described will be taken into consideration according to the conditions of use envisaged and the specific construction of the scissors.

In the case of an electrically insulated design of the insert 144 comprising the two sleeves 112, 114, the pivoting device 106 itself can be made of metal and this considerably reduces production costs for it, as already mentioned. In this particularly preferred case, a high electrical breakdown or disruptive strength is achieved by means of the insulating insert 144 extending through the two holes 108, 110 in the scissor arms 102, 104 and comprising the two sleeves 112, 114. The materials mentioned in conjunction with the first exemplary embodiment and an electrically insulating plastic can be used as electrically insulating materials for the sleeves 112, 114.

Alternatively, the sleeves 112, 114 may be a metal which is coated with an electrically insulating layer. By way of example, sleeves 112, 114 may be constructed using aluminum or alloy thereof, said aluminum alloy being hard anodized to provide electrically insulating oxide layer on surface of sleeves 112, 114. In a second exemplary construction, sleeves 112, 114 may be constructed using metallic material (e.g. stainless steel or refractory metal such as molybdenum or molybdenum alloy which is then coated with an electrically insulating coating, such as those coatings specified hereinabove with regard to screw 46 and/or nut 74.

Although this invention has been shown and described with respect to detailed embodiments thereof, it will be understood by those skilled in the art that various changes in form and detail thereof may be made without department from the spirit and scope of the claimed invention.

What is claimed is:

1. A pivoting device (16; 106) for two pivotally connected two electrically conductive parts (12, 14; 102, 104) of a bipolar electo-surgical device (10; 100) connected wherein the parts have opposed surfaces which are adjacent to each other and wherein the pivoting device (16; 106) and said surfaces (26, 28; 122, 130) of the two parts (12, 14; 102, 104) are electrically insulated from one of the parts (12, 14, 102, 104), wherein the pivoting device (16; 106) is a screwed joint which comprises a screw (46; 158) having a screw head, and a nut (74; 154), and a first hole (36; 108) in one (12; 102) of the two parts (12, 14; 102, 104) for the recessed accommodation of the screw (46; 158) and a second hole (38; 110) in the other part for the recessed accommodation of a nut (74; 154) and wherein electrically insulating material is provided at least on surfaces of the screw (46; 158) and nut (74; 154) and/or on surfaces of the holes (36, 38; 108, 110) in the two parts (102, 104) wherein the screw (46; 158) and/or the nut (74; 154) of the screwed joint (16; 106) are.

2. The pivoting device of claim 1, wherein said electrically insulating material is composed of a ceramic material.

3. The pivoting device of claim 1, characterized in that at least one portion (46; 74) of the pivoting device (16) is made from metallic material and has an outer surface and the outer surface of said at least one portion is surrounded with an electrically insulating protecting shell.

4. The pivoting device of claim 1, wherein the electrical insulation of said electrically insulating material is defined by a bulk electrical resistivity of greater than about $10_6$ ohm-cm and/or by an electrical resistance across an electrically insulating layer of greater than about 10,000 ohms.

5. The pivoting device of claim 1, wherein said electrically insulating coating is selected from the group consisting of glass, glassceramics, metal oxides, metal nitrides, metal borides and synthetic diamond.

6. The pivoting device of claim 3, wherein the at least one portion of the pivoting device is manufactured from aluminum material and the outer surface of said at least one portion is coated by means of hard anodic oxidation of aluminum material, in which aluminum oxide is formed.

7. The pivoting device of claim 6, wherein said aluminum material is AlMgSi (tief 0,5).

8. The pivoting device of claim 1, wherein the first hole (36; 108) located in one part (12; 102) and accommodating the screw head (46; 158), and the second hole (38; 110) located in the other part (14; 110) and accommodating the nut (74; 154) each have an inner annular shoulder (44, 42; 120, 128) of the same diameter, the opposite sides of which are formed by the opposed surfaces (26, 28; 122, 130) of the two pivotable parts (12, 14; 108, 110).

9. The pivoting device of claim 1, wherein the nut (74) has at least in part a smooth non-circular circumferential.

10. The pivoting device of claim 9, wherein the nut (74) has an internal through hole (86) in which is arranged an internal thread (88) matched in length to an external thread (58) of the screw (46), a front section (76) with a circular outer shape and a rear section (80) with the noncircular smooth circumferential surface.

11. The pivoting device of claim 9, wherein the noncircular circumferential surface of the nut (74, 154) is elliptical.

12. The pivoting device of claim 1, wherein the electrically insulating material is formed from a sleeve-shaped insert (144) between the surfaces of the screw (158) and nut (154) and the surfaces of the holes (108, 110) in the two parts (102, 104).

13. The pivoting device of claim 12, wherein the sleeve-shaped insulating insert (144) comprises two sleeves (112, 114) having through holes, the outside dimensions of the sleeves (112, 114) approximately corresponding to the holes (108, 110) in the two pivotable parts (102, 104), and the inside dimensions of one of the two sleeves (112, 114) are essentially matched to the outside dimensions of the screw (106), and the inside dimensions of the other of the two sleeves (112, 114) are essentially matched to the outside dimensions of the nut (154) of the screwed joint.

14. The pivoting device of claim 13, wherein the two sleeves (108, 110) each have two sections (132, 136; 134, 138) with a cylindrical outer shape, an outer sleeve section (132; 134) having a larger outside diameter than an inner sleeve section (136; 138) of both sleeves (112, 114), so that an annular shoulder (140; 142) is in each case formed between these sleeve sections (132, 136; 134, 138).

15. The pivoting device of claim 13, wherein the holes (108; 110) in the two parts (102, 104) each have two cylindrical hole sections (116, 118; 124, 136), the diameter and length of which correspond to the outer and inner sleeve sections (132, 136; 134, 138), so that the annular shoulder (120; 128) is in each case formed between the hole sections (116, 118; 124, 126), one of the two sleeves (112; 114) in each case resting on the annular shoulder by means of an outer shoulder (141; 143).

16. The pivoting device of claim 13, wherein the dimensions of the two sleeves (112, 114) of the insert (144) and the holes (108, 110) located in the parts (102, 104) are identical.

17. The pivoting device of claim 14, wherein a washer (174) is provided between the inner annular shoulder (140) of the sleeve (112) and an annular surface (166) on the underside of the head (160) of the screw (158).

18. The pivoting device of claim 17, wherein a cone angle of an upper end face (178) of the washer (174) corresponds approximately to a cone angle of a frustoconical annular surface (166) on an underside of the an screw head (160).

19. The pivoting device of claim 13, wherein the sleeves (112, 114) consist of metallic material which is provided with an electrically insulating coating.

20. The pivoting device of claim 19, wherein said sleeves (112, 114) comprise stainless steel.

21. The pivoting device of claim 19, wherein said sleeves (112, 114) comprise refractory metal.

22. The pivoting device of claim 21, wherein said refractory metal is molybdenum.

23. The pivoting device of claim 21, wherein said refractory metal is molybdenum alloy.

24. The pivoting device of claim 19, wherein the coating of said sleeves (112, 114) comprises a plasma deposited metal oxide.

25. The pivoting device of claim 19, wherein said sleeves (112, 114) are coated with chemically vapor deposited silicon nitride.

26. The pivoting device of claims 1 to 25, wherein said device is used for a bipolar electrosurgical scissor (10; 100), wherein said parts form scissor arms (12, 14; 102, 104).

* * * * *

UNITED STATES PATENT AND TRADEMARK OFFICE
CERTIFICATE OF CORRECTION

PATENT NO. : 6,406,475 B1  Page 1 of 1
DATED : June 18, 2002
INVENTOR(S) : Peter Wenzler, Philip Eggers and Andrew Eggers It is certified that error appears in the above-identified patent and that said Letters Patent is hereby corrected as shown below:

<u>Column 9,</u>
Line 23, "$10_6$" should be -- $10^6$ --

Signed and Sealed this

Nineteenth Day of August, 2003

JAMES E. ROGAN
*Director of the United States Patent and Trademark Office*